United States Patent [19]

Brown

[11] Patent Number: 4,528,842
[45] Date of Patent: Jul. 16, 1985

[54] METHOD AND APPARATUS FOR SOIL MECHANICS MEASUREMENTS OF FILTER CAKES

[75] Inventor: Mark H. Brown, Calgary, Canada

[73] Assignee: Trans-Canada Resources Ltd., Calgary, Canada

[21] Appl. No.: 655,250

[22] Filed: Sep. 28, 1984

Related U.S. Application Data

[63] Continuation-in-part of Ser. No. 594,116, Mar. 28, 1984.

[51] Int. Cl.³ .............................................. E21B 49/10
[52] U.S. Cl. ...................... 73/61.4; 73/151; 73/432 SD
[58] Field of Search .............. 73/151, 73, 432 SD, 73/61.4, 153; 166/255; 175/40

[56] References Cited

U.S. PATENT DOCUMENTS

| | | | |
|---|---|---|---|
| 2,830,266 | 4/1958 | Southwick et al. | 73/61.4 |
| 4,430,889 | 2/1974 | Sutton | 73/61.4 |
| 4,458,528 | 7/1974 | Roper et al. | 73/151 |

Primary Examiner—Stewart J. Levy
Assistant Examiner—Hezron E. Williams
Attorney, Agent, or Firm—Sim & McBurney

[57] ABSTRACT

A bore hole hydraulics simulator for drilling fluid has a pump for flowing the drilling fluid along a permeable partition which divides a first volume containing the drilling fluid from a second volume adapted to collect filtrate passing through the permeable partition. The first volume is a substantially cylindrical passageway to simulate a bore hole, having within it a rod-like member simulating a drill string. The partition is a sleeve-like insert located adjacent the rod-like member. The second volume is a chamber surrounding the insert. The rod-like member includes a device for measuring the thickness of a cake build-up on the sleeve-like insert within the passageway. The output of the pump can be adjusted in response to measurements of cake thickness, in order to maintain a substantially constant shear rate past the cake.

6 Claims, 6 Drawing Figures

METHOD AND APPARATUS FOR SOIL MECHANICS MEASUREMENTS OF FILTER CAKES

This is a continuation-in-part of U.S. patent application Ser. No. 594,116, filed on Mar. 28, 1984, and entitled "METHOD AND APPARATUS FOR SOIL MECHANICS MEASUREMENTS OF FILTER CAKES".

This invention relates generally to a method and apparatus for making particular measurements on a filter cake within an apparatus intended to simulate down-hole conditions in a drilled well. The invention set forth and claimed in the said U.S. patent application Ser. No. 594,116 has to do with improvements and additions to an apparatus described in co-pending U.S. patent application Ser. No. 551,343, filed on Nov. 14, 1983, and entitled "BORE-HOLE HYDRAULICS SIMULATOR", the latter invention being adapted to bring about the deposition of a filter cake on a permeable, cylindrical sleeve simulating a rock formation through which a well is drilled, the filter cake resulting from deposition of the solid phase while the fluid phase passes through the permeable sleeve, as the fluid is driven to move from a high pressure area within the sleeve to a lower pressure area in a compartment exterior to the sleeve.

More particularly, the invention set forth in U.S. patent application Ser. No. 594,116, of which this is a continuation-in-part, relates to a method and apparatus adapted to determine soil mechanics properties of a drilling fluid filter cake, and additionally has the ability to bring about asymmetric flow of the fluid thus likely giving rise to a filter cake of varying thickness. The apparatus has additionally the capability of determining the thickness profile of such a filter cake.

This application introduces a further concept pertaining to the simulation of down-hole conditions in a drilled well. This concept relates to the desirability of controlling the velocity of flow within a certain portion of the apparatus.

BACKGROUND OF THIS INVENTION

As is well known, drilling fluid is utilized in well-drilling operations for a number of basic purposes. One purpose is to cool and lubricate the bit and the string. Another is to carry up to the surface the bore hole material which is produced as a result of the drilling operation. A third purpose is to deposit a tough and low-permeability filter cake against the sides of the bore-hole and thus reduce the invasion of the fluid phase into the formation and control fluid losses down hole. A fourth is to overbalance formation pore-pressures with sufficient hydrostatic head in order to control well flowing. A fifth is for control of corrosion of the drill string and bit. A sixth is to buoyantly support the drill string.

Due to geothermal heat in the surrounding formations, the temperature of the drilling fluid can rise as high as 600° F. or more. The pressure of the drilling fluid is a function of depth and density. For very deep wells, the pressure of the drilling fluid at the bottom of the well can be as high as 20,000 psi or more.

It is very important for the drilling fluid not only to deposit a low permeability filter cake on the borehole wall, but one which is sufficiently tough and cohesive to resist erosion by the upwardly flowing drilling fluid in contact with the borehole walls.

The co-pending U.S. application Ser. No. 551,343, filed Nov. 14, 1983, is directed to an apparatus which comprises a main housing, a permeable cylindrical sleeve fixed with respect to the main housing and simulating a rock formation through which a well is drilled, first means defining a compartment exterior to the sleeve, second means for introducing into the interior of the sleeve a solids-containing fluid and for raising the fluid to a pressure higher than the pressure in the compartment, whereby the fluid passes through the sleeve and into the compartment, leaving a filter cake on the inside of the sleeve, and a probe extending through the sleeve and simulating a drill string. The apparatus is capable of depositing a filter cake and of making various measurements under controlled hydraulic regimes.

The invention set forth in the parent U.S. application Ser. No. 594,116 (of which this is a continuation-in-part) pertains to an apparatus for cooperation with the apparatus just described, which allows a determination of the soil mechanics properties of the filter cake, and the profile of filter cake thickness measured circumferentially around the sleeve. The apparatus is also capable of off-centering the probe, which may induce a non-uniform filter cake thickness.

One of the capabilities of the apparatus described in both of the aforesaid applications is that of determining the resistance of the filter cake to erosion by the flowing stream of drilling fluid. The drilling fluid is made to flow through the permeable cylindrical sleeve by a recirculating pump, typically a positive displacement pump, and this forced flow carries the drilling fluid along the surface of the forming filter cake.

If the volumetric flow setting of the pump were to remain constant while the filter cake gradually built up against the permeable cylindrical sleeve, the cross-section at the sleeve available for flow would constantly decrease, thus causing higher and higher velocities of the drilling fluid past the filter cake. In actual drilling conditions the flow speed and the shear rate at the outside surface of the filter cake tend to be constant, as long as rheological properties, hole size, pipe size and flow rate remain constant. Thus, in order to improve the simulation of down-hole conditions, the shear rate at the surface of the filter cake in the simulator should remain constant, regardless of filter cake build-up.

GENERAL DESCRIPTION OF THIS INVENTION

In view of the foregoing discussion, it is an object of an aspect of this invention to provide a method and apparatus adapted to simulate down-hole conditions in a drilled well, including the maintenance of a substantially constant shear rate past the filter cake.

More particularly, this invention provides a bore hole hydraulics simulator for drilling fluid which includes a pump for flowing the drilling fluid along a permeable partition which divides a first volume containing the drilling fluid from a second volume adapted to collect filtrate passing through the permeable partition. The first volume is a substantially cylindrical passageway to simulate a bore hole, having therewithin a rod-like member to simulate a drill string. The partition is a sleeve-like insert located adjacent the rod-like member. The second volume is a chamber surrounding the insert. Means are associated with the rod-like member for measuring the thickness of a cake build-up on the sleeve-like insert within the passageway. Means are provided for adjusting the output of the pump in response to measurements of cake thickness, in order to maintain a substantially constant shear rate past the cake.

This invention further provides a method of testing the properties of a drilling fluid under dynamic conditions, comprising the steps: Flowing the drilling fluid within a permeable sleeve which divides a first volume inside the sleeve from a second volume external to the sleeve, the second volume being adapted to collect filtrate passing through the permeable sleeve, the sleeve having a rod-like member therewithin to simulate a drill string. A pressure differential is placed across the sleeve so as to promote the passage of filtrate into said second volume and the deposition of a filter cake on the inside of the sleeve. Filtrate passing into said second volume is collected. The thickness of the filter cake on the sleeve is detected at time intervals. On the basis of the determined filter cake thickness, the quantity flow rate of the drilling fluid within the sleeve is controlled in order to maintain a substantially constant shear rate past the cake.

GENERAL DESCRIPTION OF THE DRAWINGS

One embodiment of this invention is illustrated in the accompanying drawings, in which like numerals denote like parts throughout the several views, and in which.

DETAILED DESCRIPTION OF THE DRAWINGS

Figure 1A:
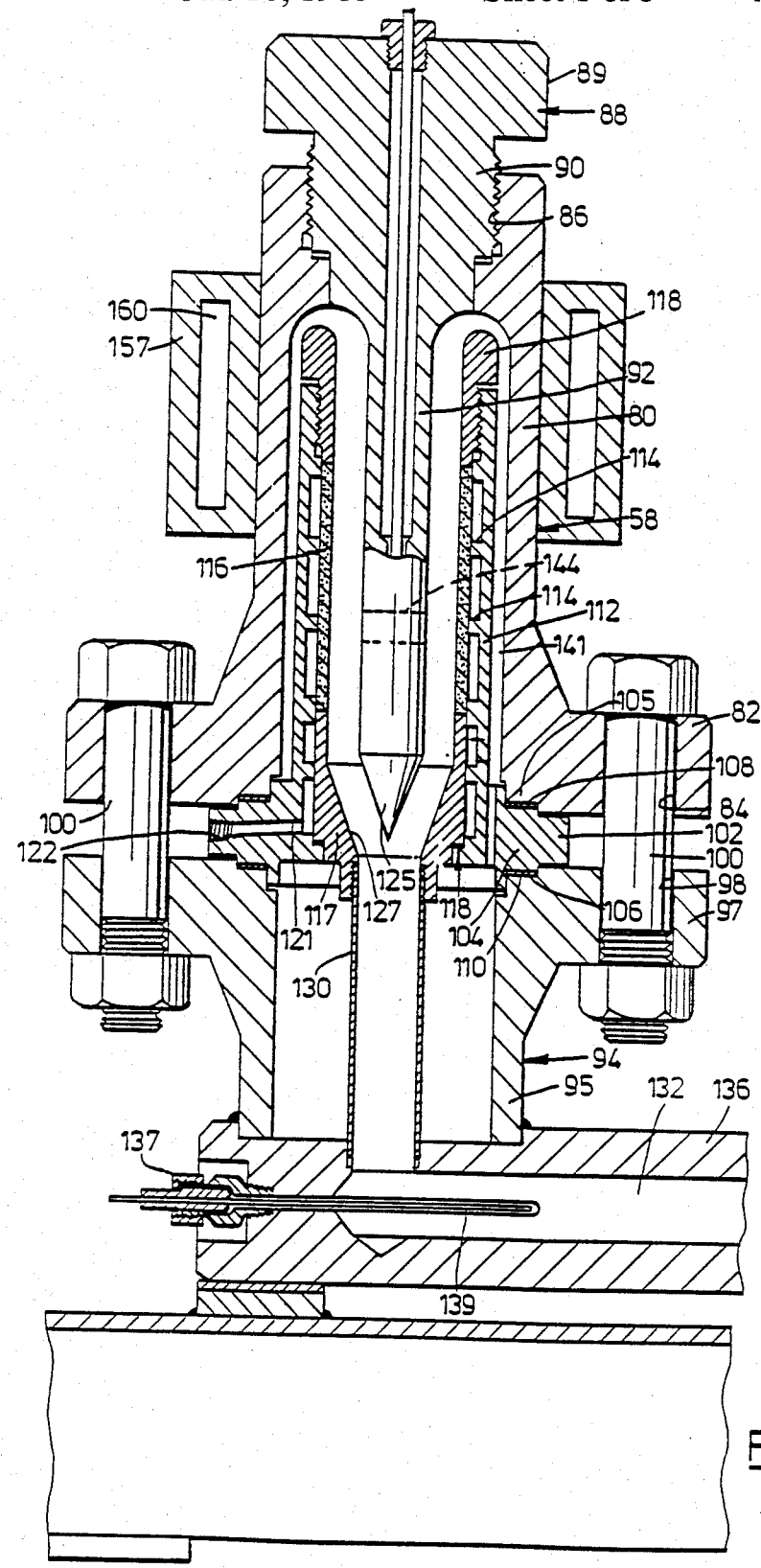
FIG. 1 (broken into 1A and 1B) is a sectional view through a filtration unit, including a circulating pump means, disclosed and claimed in copending U.S. patent application Ser. No. 551,343, filed on Nov. 14, 1983.
Figure 1B:
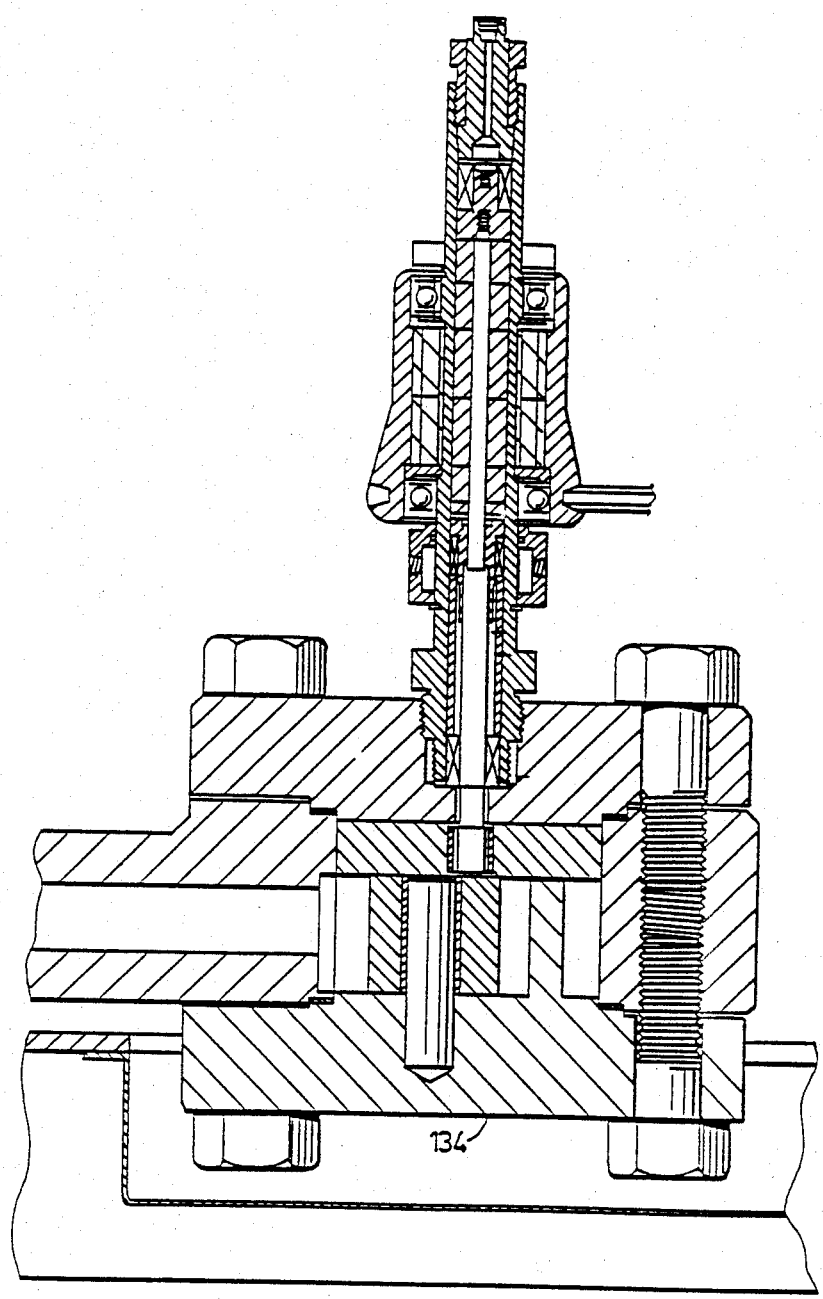

Attention is first directed to FIG. 1, which shows a fluid testing vessel 58 to include a main cylindrical body 80 having a flange 82 for clamping purposes, the flange 82 being provided with a plurality of circumferentially separated bolt holes 84. At the top, the cylindrical member 80 has a threaded bore 86 adapted to receive a plug 88 having a hexagonal top portion 89, a screw-threaded portion 90, and a probe 92, the purpose of which will be explained subsequently. The fluid testing vessel 58 also includes a base member 94 having a downwardly projecting cylindrical portion 95 and a flange 97, the flange having bolt holes 98 corresponding to the bolt holes 84 in the flange 82, such that when the bolt holes are in alignment, a plurality of bolts 100 can be placed therethrough in order to tighten the flanges together. The flanges sandwich between them an insert member 102 having a stepped portion 104 for cooperation with stepped portions 105 and 106 of the cylindrical member 80 and the base member 94, respectively. As can be seen in the figure, annular gaskets 108 and 110 are provided as seals between the various members. The insert 102 includes an upstanding cylindrical portion 112 which comprises inwardly extending ridges 114 adapted to support from the outside a porous, cylindrical sleeve 116 which is sandwiched between an upper plug 118 which has a threaded engagement with the top part of the cylindrical portion 112, and a further insert 117 which has a stepped engagement at 118 with the insert 102. Gaskets are provided at the top and bottom of the cylindrical sleeve 116, these being adapted to cushion the sleeve 116 against excessive loading. It is contemplated that the sleeve 116 be constituted of sintered metal, porous ceramic material, or the like, and it is known that certain of these materials can be very brittle. The cylindrical sleeve 116 could also be machined from a sample of the actual rock being drilled, depending upon the strength of the rock.

The space between the porous cylindrical sleeve 116 and the cylindrical portion 112 of the insert 102 exists by virtue of the spacing provided by the ridges 114. The ridges 114 are not continuous, and therefore the entire volume between the cylindrical sleeve 116 and the cylindrical portion 112 can be considered a single volume. This volume is in communication with an outlet duct 121, which has a pipe-threaded female connecting portion 122, to which a suitable conduit can be connected. The probe 92 extends centrally downwardly within the plug 118, the porous cylindrical sleeve 116, and the upper part of the further insert 117. Furthermore, the probe 92 has a conically tapered lower end 125, in order to facilitate passage of drilling mud around and along the probe 92. Moreover, the further insert 117 has an internal frusto-conical wall 127, again for promoting smooth flow of the drilling mud.

Below the further insert 117, and within the base member 94, a pipe 130 is provided, the pipe 130 connecting with the passage that surrounds the probe 92, and at its lower end connecting with a delivery passageway 132 from a positive displacement pump 134 of known construction. The annular space around the pipe 130 and within the base member 94 constitutes part of a suction passageway for drilling mud, which leads (by a passageway which is not cut by the section shown in FIG. 1) to the suction side of the positive displacement pump 134. The passageway 132 is defined in a horizontally elongated member 136, into which a mounting means 137 projects a temperature probe 139. The annular passageway between the pipe 130 and the base member 94 connects with a further annular passageway 141 exterior of the cylindrical portion 112 but within the cylindrical member 80, this annular passageway communicating with the top of the passageway between the probe 92 and the porous cylindrical sleeve 116.

Mounted within the probe 92 is an ultrasonic device 144, which includes an ultrasound generator and an ultrasound receiver, capable of determining the mud cake thickness on the inside wall of the porous cylindrical sleeve 116, during operation.

The ultrasonic device is capable of generating an ultrasound signal in the direction radially outwardly from the probe 92, and this signal then is reflected back by caked mud on the porous cylindrical sleeve 116. The length of time taken for the echo to be picked up by the receiver can be used to determine the thickness of the mud cake.

An aluminum block 157 of cylindrical configuration surrounds the cylindrical member 80, and contains within it a conventional heating means, such as a cal-rod, in the interior 160, this being for the purpose of maintaining the filter cake deposition area at a desired elevated temperature.

Figure 2:
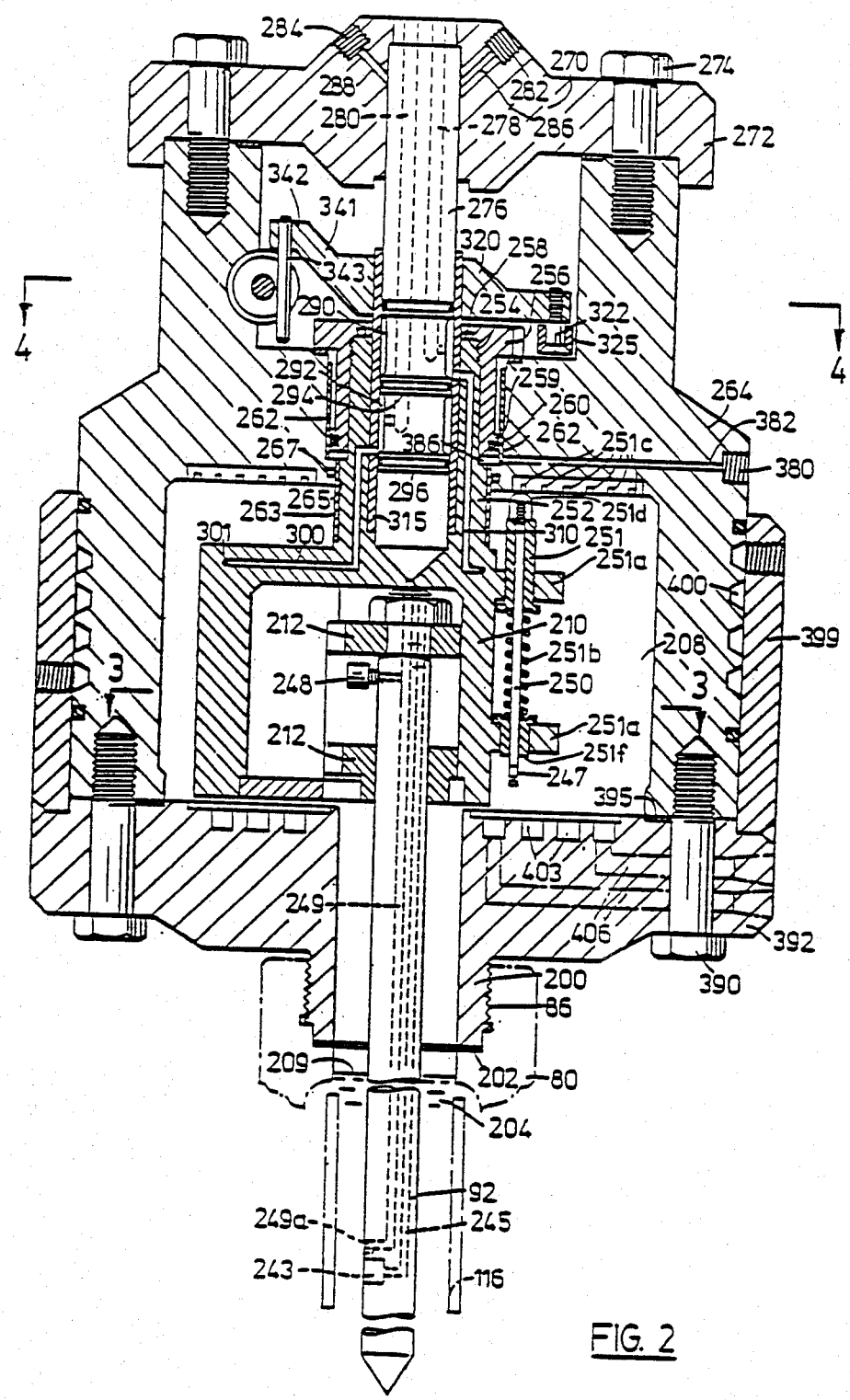
FIG. 2 is an axial sectional view through a apparatus adapted to be affixed to the apparatus shown in FIG. 1, and capable of performing stickometric measurements on a filter cake.

Attention is now directed to FIG. 2, in which the upper portion of the cylindrical member 80 is shown in chain-dotted lines. The internal threads 86 of the member 80 are engaged by a boss 200 which contacts a seal 202 that prevents access to the threads 86 from the annular space surrounding the probe 92. The annular space surrounding the probe 92, shown in FIG. 2 by the numeral 204, has access upwardly to a compartment 208 in which is located a body 210 which may undergo rotation within the compartment 208 and may also move longitudinally in the direction of the axis of the probe 92, by virtue of mechanisms which will be described subsequently. The compartment 208 is filled with nitrogen under pressure, which extends down to the liquid/$N_2$ interface 209.

Figure 4:
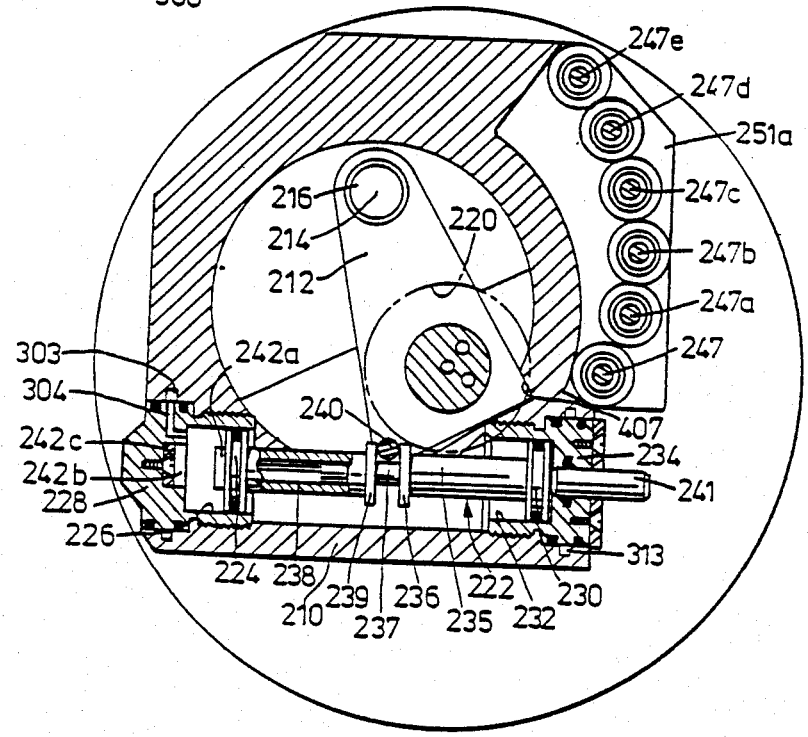
FIG. 4 is a cross-sectional view taken at the line 3—3 in FIG. 2.

As can be seen by looking simultaneously at FIGS. 2 and 4, the upper end of the probe 92 is supported by two axially spaced-apart brackets 212 which are pivoted about an axis identified in FIG. 4 by the numeral 214 and defined by a pin 216 which is journalled with respect to the body 210. As can be particularly well seen in FIG. 4, the brackets 212, which are pivotally mounted with respect to the pin 216, can shift together and carry the probe 92 in an arcuate path toward and away from the wall of the sleeve 116, shown in chain-dotted lines in FIG. 2. The inside surface of the sleeve 116 is identified at 220 in FIG. 4.

Shown in FIG. 4, but not intersected by the section of FIG. 2, is a hydraulically operated composite piston 222 which is double ended, one end 224 sliding in a cylinder 226 defined by a threaded insert 228, the other end 230 sliding in a cylinder 232 defined by an insert 234. The inserts 228 and 234 are threaded into appropriate threaded bores in the body 210. The end 230 is integral with a shaft 235 which has a land 236 and has a smaller-diameter coaxial extension 237. The extension is slidably received in a bore in a shaft 238 integral with the end 224. The shaft 238 has a land 239, and the two lands 236 and 239 capture between them an upstanding rod 240 extending between the two brackets 212. An ultrasonic probe 241 is mounted in the insert 234, the purpose of which is to allow a determination of the position of the piston 222.

The end 224 has affixed thereto a permanent magnet 242a, and a similar magnet 242b is affixed to a machine screw 242c which is screwed into the insert 228.

The probe 92 has mounted therein an ultrasonic generator and receiver shown in broken lines at 243, from which an electrical wire passes upwardly along a vertical bore 245 in the probe 92, and exits at the top thereof, above the uppermost bracket 212. From there, the wire loosely passes to one end of an access bore (not shown) through which it extends to connect to a contact 247 which is mounted to the body 210 and rotates therewith. A pressure transducer 248 is mounted to the probe 92 within the body 210 and communicates along passage 249 with an opening 249a in the side of the probe 92, adjacent the sleeve 116. The transducer 248 is connected via another wire to a contact 247a (see FIG. 4), also secured to rotate with the body 210. The wires have some slack in them to permit the brackets 212 to move the probe 92 toward and away from the interior wall of the sleeve 116.

A plurality of contacts 247-247e are provided, each consisting of a rod 250 sliding within an insulator guide 251 and threaded into a contact 251d. The rod and guide slide within two guide flanges 251a and a spring 251b biases them upwardly into contact with one of a plurality of concentric slip rings 251c. The rod 250 slides within a further insulator guide 251f supported in a bore within the lower guide flange 251a. Electrical connections (not shown) extend from the slip rings 251c to the exterior of the apparatus shown in FIG. 2.

The body 210 is integral with an upstanding boss portion 252, the upper end of which is threaded at 254 into a ratchet wheel member 256. An O-ring seal is provided at 258 between the boss portion 252 and the ratchet wheel member 256.

The ratchet wheel member 256 defines a piston 259 at the bottom, having an O-ring seal 260 which rides against a cylindrical insert 262 internally of a main housing member 264. The insert may typically be of polished bronze.

Below the ratchet wheel member 256, the boss portion 252 has a cylindrical polished sleeve 263, similar to the insert 262, secured thereto. The sleeve 263 is adapted to move axially and radially within a circular opening 265 in the main housing member 264, equipped with an O-ring seal 267.

Extending downwardly from a cap portion 270 which is secured to the main housing member 264 at a flange 272 by virtue of machine bolts 274, is a stationary shaft 276, having two internal bores 278 and 280, each of which communicates with a separate tapped bore 282 and 284, respectively, through drilled passageways 286 and 288, respectively. The drilled bores 282 and 284 are adapted to receive connectors, so that hydraulic lines can be placed into communication with the bores 278 and 280.

As can be seen in FIG. 2, the lower end of the shaft 276 is provided with a first gallery region 290 and a second gallery region 292, these being spaced axially from one another, and separated by a land 294. Below the gallery region 292 is a further land 296, and both of the lands 294 and 296 are provided with an O-ring seal. Similarly, an O-ring seal is provided immediately above the gallery region 290. This allows the definition of two annular compartments, the one being adjacent the gallery region 290, the other being adjacent the gallery region 292. The annular compartment adjacent gallery region 290 is in communication with the bore 278, and the annular compartment adjacent the gallery region 292 is in communication with the bore 280.

In FIG. 2, the body 210 and boss portion 252 are shown in their lowermost position, it being understood that they can rise from that position over a distance permitted by the height of the compartment 208 above the body 210. As seen in FIG. 2, the annular compartment adjacent the gallery region 292 communicates along a passageway 300 with a horizontal passageway 301 which extends in the direction perpendicular to the drawing plane, and which in turn communicates through a vertical passageway (not seen) with an annular gallery 303 surrounding the insert 228 (see FIG. 4). From the gallery 303, a bore 304 communicates with the chamber within the cylinder 226. A similar passageway 310 communicates with the annular compartment adjacent the gallery region 290, and by a like arrangement communicates ultimately with the compartment defined within the cylinder 232, through a gallery 313.

Hence, it will be understood that, regardless of the rotational or vertical orientation of the body 210, the threaded bores 282 and 284 are always in communication with the cylinders 232 and 226, respectively, whereby the position of the piston 222 can be controlled.

It will be seen in FIG. 2 that a cylindrical insert 315 is provided inside the boss portion 252, and runs in contact with the O-ring seals in the lands 294 and 296, as well as the O-ring seal above the gallery region 290.

Mounted for rotation about the central axis of the shaft 276, and riding against the cylindrical insert 315 is a pawl arm 320, which supports a stub shaft 322 from which a pawl 325 is pivoted. The pawl 325 is spring biased so that its operative end 326 seeks to engage the teeth 327 of the ratchet wheel member 256. The main housing 264 pivotally supports a further pawl 334 which turns about a threaded pin 336 that is fixed with respect to the main housing member 264. The pawl 334 has a contact end 339 which likewise contacts the teeth 327 of the ratchet wheel member 256, due to the fact that the pawl 334 is spring biased in the clockwise sense (spring not shown).

As can be seen in FIG. 2, the pawl arm 320 undergoes an oblique upward step at 341 and terminates in an elevated portion 342 from which downwardly extends a pin 343.

Figure 3:
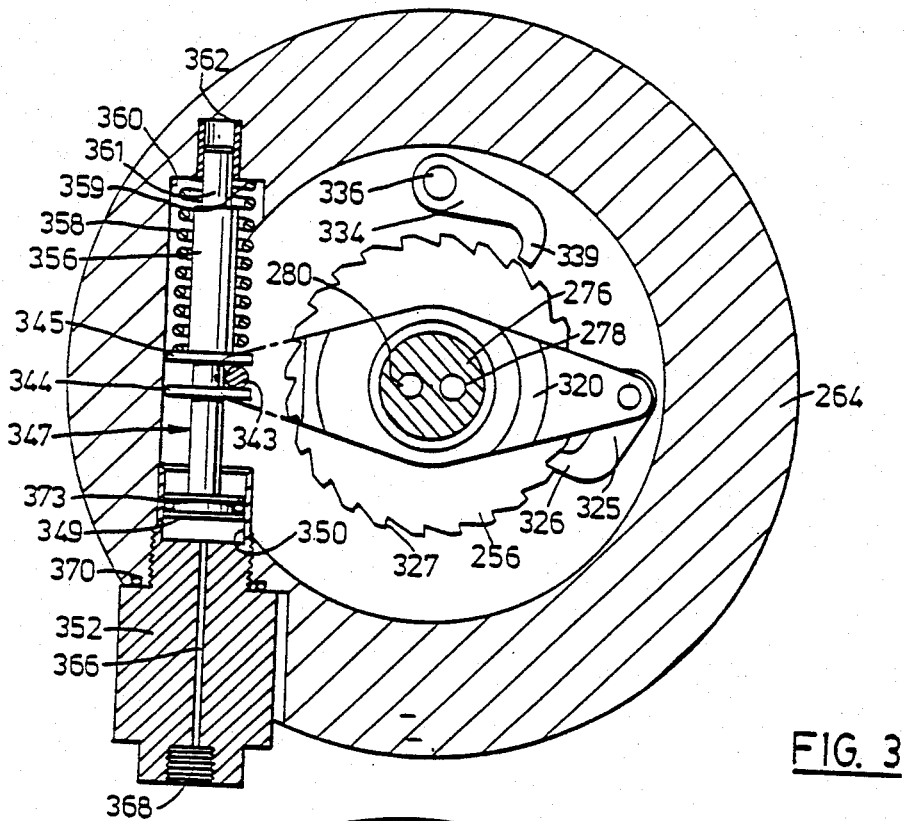
FIG. 3 is a cross-sectional view taken at the line 4—4 in FIG. 2.

As now seen in FIG. 3, the pin 343 is captured between two lands 344 and 345 of a hydraulically operated piston 347 having one end 349 riding within a cylinder 350 defined by a threaded insert 352, and having the other end 356 shaped to receive one end of a compression spring 358, of which the other end bears against the end wall 359 of a cylindrical recess 360. The end 356 of the piston 347 has a reduced extension 361 slidably engaging a sleeve 362 in a continuation of the recess 360. A passageway 366 communicates the chamber defined by the cylinder 350 with a threaded bore 368. An O-ring seal 370 is provided for the insert 352, and the portion 349 of the piston 347 is also provided with an O-ring seal 373.

It will be appreciated that, by pressurizing the compartment defined by the cylinder 350, the hydraulically-operated cylinder 347 can be caused to move upwardly in FIG. 3 against the urging of the compression spring 358, thus rotating the pawl arm 320 in the clockwise sense as seen in FIG. 3, thus causing the pawl 325 to urge the ratchet wheel member 356 also in the clockwise sense. When an angular movement the equivalent of one tooth has been undergone, the other pawl 334 will lodge behind the tooth and prevent return motion of the ratchet wheel member, so that the pawl arm 320 can return to the original position and allow the pawl 325 to lodge behind the next tooth. By sending repeated pulses to the chamber defined by the cylinder 350, the ratchet wheel member 356, and thus the body 210, can be rotated to any desired position in a rotational sense.

In order to raise the body 210 upwardly, hydraulic pressure is admitted through a threaded bore 380, along a passageway 382, and into a compartment 386 below the ratchet wheel member 256, and in particular below the piston 259 defined at the bottom of the ratchet wheel member 256. Gravity is used to allow the body 210 to descend.

Machine bolts 390 secure a flange 392 integral with the boss 200 to the main housing member 264, with the provision of a circular seal 395 to seal the compartment 208. The flange 392 is secured to an upstanding shell 399 which defines a spiral cooling passage 400 with the main housing member 264, into which the appropriately shaped groove is machined.

Similarly, a spiral passage seen in section at 403 in FIG. 2 allows for additional temperature control, through passageways identified generally by the numeral 406. This provision allows a significantly lower temperature in compartment 208 than in the test fluid.

The attachment apparatus described with reference to FIGS. 2, 3 and 4 may be utilized for a number of different functions, as follows.

Firstly, in order to simulate an off-centre drill string down a well-bore, it is merely necessary to move the probe 92 to an intermediate position between the axially centred position shown in FIG. 2 and a position in which it is in contact with the interior surface of the sleeve 116. Then, the apparatus shown in FIG. 1 is placed into operation in order to cause a filter cake to be deposited on the inside surface of the sleeve 116. Because of the off-centre positioning of the probe 92, it will be appreciated that the flow rates of the fluid toward and through the sleeve 116 will be different for different peripheral locations around the sleeve. This in turn will cause variable deposition and erosion rates for the filter cake.

It will be appreciated that the piston 222 can be moved to the left in FIG. 4 by admitting pressurized fluid along passageway 310 to the chamber within bore 232 to the right of the end 230. This urges the probe 92 leftwardly to assume an off-centre position. If the probe 92 is not in contact with the interior wall of the sleeve 116, the slidable relation between the shafts 235 and 238 will permit leftward drifting of the probe, should a differential pressure arise due to differing flow rates around its periphery. If the probe 92 should seek to approach the closer side of the sleeve 116, the leftward piston end 224 could be moved back to the right to establish a stop or limit to this approach.

When it is desired to allow differential pressure on the probe 92 to move it against the filter cake, the piston 222 is used to bring the probe to a close approach, at which point the magnets 224 and 224b attract each other and withdraw the land 239 out of interfering relation with the probe, thus leaving it free to move leftwardly. This arrangement is utilized when seeking to test the stickometric properties of the filter cake, since the removal of the land 236 out of the way prevents it from interfering with encroachment of the probe 92 into the filter cake, regardless of where the rightward end 230 of the piston 222 is located at the time.

It will be appreciated that, in the arrangement shown in FIG. 4, the piston 224 is capable of locking the probe 92 in a centred position with respect to the interior surface 220 of the sleeve 116, by virtue of the fact that the brackets 212 lodge at their rightward corners against a stop 407 which is machined into the interior of the body 210. In FIG. 4 the components are shown in the position in which the probe 92 is in this blocked condition.

In order to determine the filter cake profile around the periphery of the sleeve 116, the apparatus of FIG. 2 is operated first to return the probe 92 to its centred position with respect to the sleeve 116, and then the ratchet apparatus at the top of the body 210 (shown in section in FIG. 3) is operated to progressively rotate the probe about its centre axis (coaxial with the sleeve 116), while the ultrasonic device 243 takes soundings by echoing an ultrasound pulse from the surface of the filter cake deposited on the inside surface of the sleeve 116. A suitable electronic apparatus (not shown) can be employed to interpret the electronic signals thus generated, and (if desired) display the resultant filter cake profile on a screen.

It will be appreciated that the profile of the filter cake can be taken at more than a single horizontal level, due to the ability of the probe to be raised.

If it is desired to test the stickometric properties of a filter cake, the filter cake is first deposited in the normal way, typically with the probe 92 on centre with respect to the sleeve 116. Then, the piston 222 is activated by applying hydraulic pressure within the chamber defined by the cylinder 232, to move the piston 222 to the left as seen in FIG. 4, thus bringing the land 237 into contact with the rod 240, thus rotating the brackets 212 in the clockwise sense about the axis 214 and carrying the probe 92 toward the interior wall of the sleeve 116. It will be appreciated, from an inspection of FIG. 4, that the probe 92 will approach the interior surface of the sleeve 116 substantially normally, partly due to the substantial length of the swing arm from the pivot axis 214 to the probe 92. From the ultrasonic sounding previously taken, an accurate idea may be had as to the specific location of the surface of the filter cake. The piston 222 is moved just far enough to bring the probe 92 into the vicinity of contact with the filter cake, but does not force the probe into the filter cake. Because the land 239 is magnetically withdrawn to the left, the entire force causing the probe 92 to enter the filter cake arises due to the differential pressure between the interior of the sleeve 116 and the cavity which surrounds the sleeve 116. This differential pressure will cause the probe to be urged tightly into the filter cake, and it will become stuck in this position to a greater or lesser degree, depending upon the characteristics of the filter cake itself.

In order to test the force necessary to release the probe 92 from its stuck position with respect to the filter cake, hydraulic pressure is applied through the passageway 382 to a location below the piston 259 defined at the bottom of the ratchet wheel member 256. The pressure is gradually increased until the probe moves, and in this manner the threshold force required can be determined.

In order to determine the threshold force just mentioned, the pressure of the hydraulic fluid in passageway 382 is monitored, and it will be found that there is a spike in the pressure at the point when movement begins. This pressure spike will indicate the hydraulic pressure just prior to breaking the probe free of the filter cake, and from that pressure the force seeking to lift the probe at the point of release can be calculated.

To determine the filter pore pressure where the same is contacted by the probe 92, the reading provided by the transducer 248 is monitored as the probe 92 encroaches into the filter cake. The opening 249a is located on the mid-line of contact between the probe 92 and the filter cake.

In accordance with the present invention, the quantity output of the positive displacement pump 134 is controlled in such a way that the shear rate of the drilling fluid past the porous cylindrical sleeve remains substantially constant.

This procedure is accomplished by utilizing a feedback loop principle, in which the filter cake thickness is measured at time intervals, preferably by using the ultrasonic generator and receiver shown in broken lines at 243, and the measurements are utilized to compute the shrinking cross-section within the sleeve 116 as the filter cake increases in thickness. The output of the pump is then adjusted so that the shear rate of drilling fluid past the sleeve 116 is substantially constant. The computations and the control can easily be carried out by a computer or similar device, the design of which would be within the competence of the skilled designer.

Figure 5:
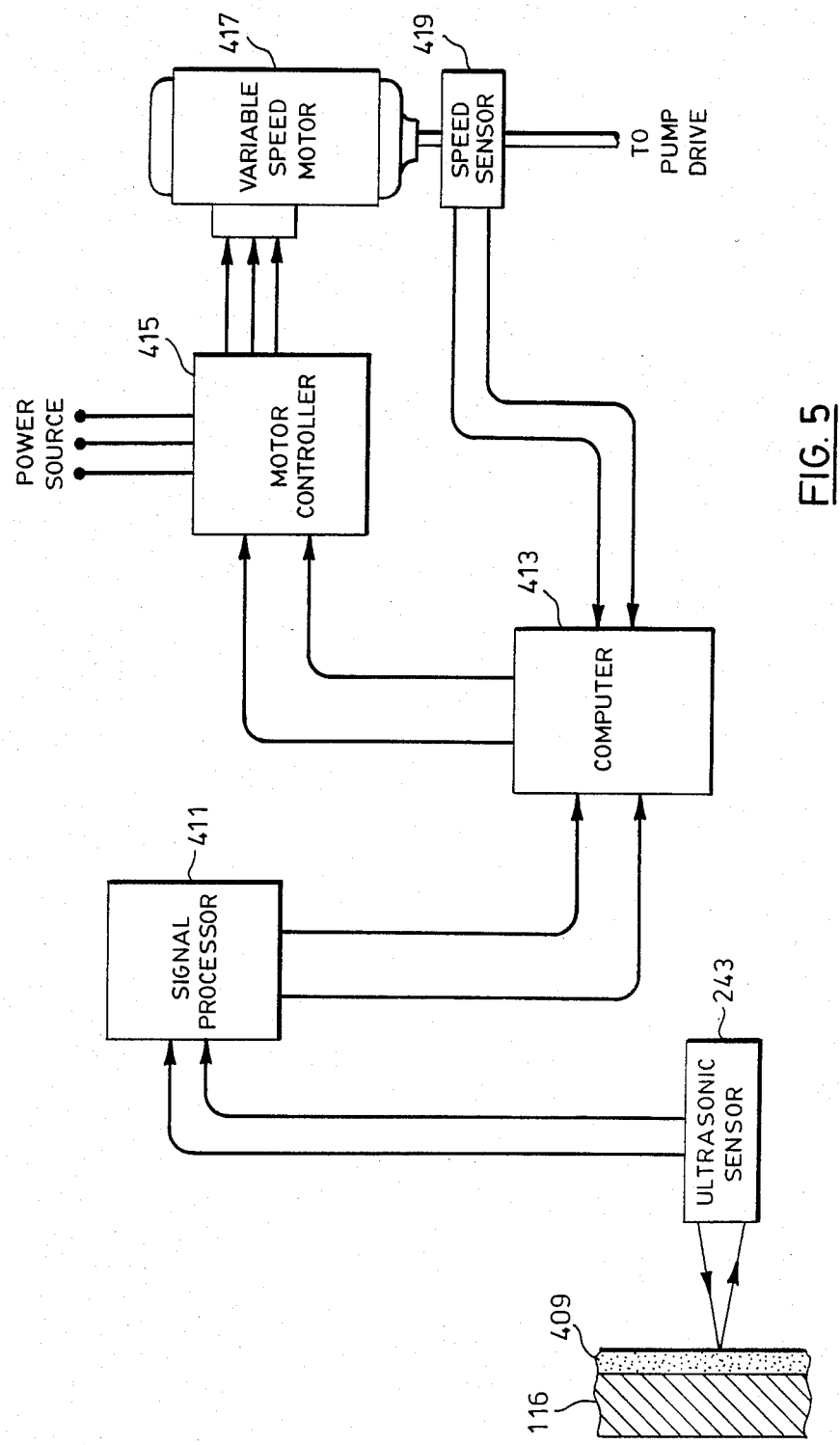
FIG. 5 is a schematic drawing of the main components of the feed-back loop control system in accordance with this invention.

Attention is now directed to FIG. 5 which illustrates schematically a suitable feed-back loop system for accomplishing control of the drilling fluid flow velocity in the manner just described. In FIG. 5, the block 243 is the ultrasonic sensor also identified by the same numeral in FIG. 2. The filter element constituted by the cylindrical sleeve 116 is shown at the left in FIG. 5, and the numeral 409 designates a filter cake build-up on the cylindrical sleeve 116. The ultrasonic sensor sends a signal across the intervening liquid to the surface of the cake 409, and then receives the echo from that signal. Both the sending and the receiving pulses are passed to a signal processor 411, which converts the impulses from the sensor 243 into a form that can be read by a computer 413 or the like. The computer controls a motor controller 415 which receives power from a power source and which in turn controls the speed of a variable speed motor 417 which controls the positive displacement pump 134 (seen in FIG. 1B). A speed sensor 419 on the output shaft of the variable speed motor 417 senses the speed at any given time, and signals this speed to the computer 413. The feed-back loop thus provided permits the computer 413 to control the speed of the variable speed motor 417 in such a way as to maintain a substantially constant shear rate of drilling fluid past the filter cake 409, as the filter cake changes in thickness.

In the appended claims, the word "fluid" is used to include the drilling mud or other test material of which certain properties can be determined by the apparatus and method herein disclosed. It is also conceivable that a foam material could be utilized in place of the drilling mud, the foam thus not being a liquid strictly speaking. It is for this reason that the term "fluid" is believed more appropriate in the claims.

While one embodiment of this invention has been illustrated in the accompanying drawings and described in the foregoing disclosure, it will be apparent to those skilled in the art that changes and modifications may be made therein without departing from the essence of the invention, as set forth in the appended claims.

What I claim is:

1. A bore hole hydraulics simulator for drilling fluid comprising: a pump for flowing the drilling fluid along a permeable partition which divides a first volume containing the drilling fluid from a second volume adapted to collect filtrate passing through the permeable partition, the first volume being a substantially cylindrical passageway to simulate a bore hole, having therewithin a rod-like member to simulate a drill string, the partition being a sleeve-like insert located adjacent the rod-like member, the second volume being a chamber surrounding the insert, means associated with the rod-like member for measuring the thickness of a cake build-up on the sleeve-like insert within the passageway; and means for adjusting the output of the pump in response to measurements of cake thickness, in order to maintain a substantially constant shear rate past the cake.

2. The invention claimed in claim 1, in which the rod-like member may be eccentrically positioned within the insert.

3. The invention claimed in claim 1, in which the means for measuring the thickness of a cake build-up is an ultrasonic device within the rod-like member.

4. The invention claimed in claim 1, in which the pump is a positive displacement pump.

5. A method of testing the properties of a drilling fluid under dynamic conditions, comprising the steps:

flowing the drilling fluid within a permeable sleeve which divides a first volume inside the sleeve from a second volume external to the sleeve, the second volume being adapted to collect filtrate passing through the permeable sleeve, the sleeve having a rod-like member therewithin to simulate a drill string, placing a pressure differential across the sleeve so as to promote the passage of filtrate into said second volume and the deposition of a filter cake on the inside of the sleeve, collecting the filtrate passing into said second volume, detecting the thickness of the filter cake on the sleeve at time intervals, and on the basis of the determined filter cake thickness controlling the quantity flow rate of the drilling fluid within the sleeve to maintain a substantially constant shear rate past the cake.

6. The method claimed in claim 5, in which the step of detecting the thickness of the filter cake is carried out ultrasonically by a device within the rod-like member.

* * * * *